United States Patent
Chau

(10) Patent No.: US 6,453,949 B1
(45) Date of Patent: Sep. 24, 2002

(54) PLUG FOR MEDICAL BAYONET CONNECTORS AND DRUG INFUSION PORTS

(76) Inventor: Sam Chau, 7407 Timber Ridge Trail, Sugarland, TX (US) 77479

(*) Notice: Subject to any disclaimer, the term of this patent is extended or adjusted under 35 U.S.C. 154(b) by 0 days.

(21) Appl. No.: 09/925,175

(22) Filed: Aug. 8, 2001

(51) Int. Cl.$^7$ .................................................. F13L 55/10
(52) U.S. Cl. ........................ 138/89; 138/96 T; 215/356; 220/295; 220/297; 220/300; 604/256
(58) Field of Search ................................ 138/89, 96 R, 138/96 T; 215/357, 356; 220/243, 296, 297, 300, 295; 604/256

(56) References Cited

U.S. PATENT DOCUMENTS

| | | | |
|---|---|---|---|
| 3,913,783 A | * 10/1975 | Cooper | 220/300 |
| 4,564,054 A | 1/1986 | Gustavsson | 141/329 |
| 4,673,404 A | 6/1987 | Gustavsson | 604/411 |
| 4,785,859 A | 11/1988 | Gustavsson et al. | 141/313 |
| 4,857,062 A | * 8/1989 | Russell | 138/96 R |
| 5,694,978 A | * 12/1997 | Heilmann et al. | 138/89 |

* cited by examiner

Primary Examiner—Patrick Brinson
(74) Attorney, Agent, or Firm—Kenneth A. Roddy

(57) ABSTRACT

A plug and sealing system for medical bayonet connectors and drug infusion ports of the type having an interior self-sealing element. A male plug removably installed in the female collar portion of the connector, before or after penetration of the self-sealing element by a puncturing needle, has a shank portion the fits the inner surfaces of the collar portion side wall to provide a substantial sealing relation therebetween to prevent contamination of the interior surfaces of the collar portion from environmental contaminants. The plug has a bottom end that is resiliently engaged on an outer face of the self-sealing element, and a pair of lugs that are resiliently biased against a top wall of diametrically opposed apertures in the side wall of the collar portion to maintain the bottom end in a firm sealing relation with the self-sealing element to prevent leakage and spreading of aerosols and vapor.

13 Claims, 3 Drawing Sheets

PLUG FOR MEDICAL BAYONET CONNECTORS AND DRUG INFUSION PORTS

BACKGROUND OF THE INVENTION

1. Field of the Invention

This invention relates generally to connectors used in the medical field, and more particularly to a plug and sealing system for medical bayonet connectors and drug infusion ports that will prevent contamination of the interior surfaces of the female bayonet collar from environmental contaminants and engage a self-sealing plug or membrane in the female bayonet collar in a sealing relation, before or after penetration by a puncturing needle, to prevent leakage and spreading of aerosols or vapor.

2. Brief Description of the Prior Art

Drugs for treating cancer, cytotoxic drugs, are very beneficial, however, they may cause serious problems for the medical personnel handling them. When medical personnel work with chemo and/or cytotoxic drugs, they rely on gowns and gloves to prevent contamination and safety cabinets or safety hoods to substantially filter the surrounding air in the environment of the cabinet or hood. However, new evidence has shown that cytotoxic drugs vaporize at room temperature, i.e. safety cabinets cannot protect the personnel from the dangerous vapor. Also, by contamination the drugs are found under gloves and gowns.

Those at risk to exposure include pharmacy technicians who prepare the drugs and oncology nurses that administer them to the patients and take care of the waste handling. The drugs are usually delivered to the pharmacy either as a powder or in solution. A pharmacy technician dissolves the powder in the vial and loads the solution into syringes or infusion sets, ready to be administered. The oncology nurse then administers the drug to the patient and discards the waste products.

Scientific studies have shown contamination by cytotoxic drugs on working trays, on floors, on vials and on outside surfaces of safety cabinets. Contamination is even seen on floors outside the preparation room. Once established, the contamination is almost impossible to remove or get rid of. Several studies have also shown that cytotoxic drugs are frequently found in the urine of personnel preparing and administrating them, and among personnel who are not even in contact with the vials. Some of the serious complications due to exposure to cytotoxic drugs include liver damage, leukemia, non-Hodgkin's lymphoma, skin cancer, miscarriages, malformations and children with low birthweight.

Due to the concern about the level of environmental contamination, many hospitals are implementing a closed system for the preparation and administration of cytotoxic drugs. One such system is known as PhaSeal®, manufactured by Carmel Pharma AB of Sweden, and commercially available through its U.S subsidiary, Carmel Pharma Inc., of Shelton, Connecticut. PhaSeal® is a completely sealed system for preparation, administration and waste handling. The PhaSeal® system was developed by Bengt Gustavsson, and some of the components are disclosed in U.S. Pat. Nos. 4,564,054, 4,673,404, and 4,785,859. The PhaSeal® system utilizes two key features to transfer drugs; a double membrane system, and a pressure equalization technique.

The PhaSeal® "Protector" is a vial transfer adapter cover having a bottom end that is fastened to a drug vial and has a built-in expansion chamber to equalize the pressure when diluting the drug, injecting air into the vial, or aspirating the drug. The expansion chamber significantly reduces the likelihood of vapor and aerosol leakage during preparation.

The PhaSeal® "Connector Luer Lock" is a connector that attaches to a patient's I.V. tubing to allow a sealed drug transfer for I.V. push therapy. The PhaSeal® "Infusion Adapter" is a non-vented intravascular administration connector that allows a sealed drug transfer directly into I.V. bags.

The PhaSeal® "Injector Luer" is drug transfer needle device having an encapsulated cannula that is permanently locked onto a syringe using a Luer or Luer Lock fitting. The opposed end of the cannula "Injector Luer" has a male bayonet fitting with an elastomeric A self-sealing membrane at the tip end. Sealed transfer can be made via the "Injector Luer" in both the preparation and administration. The expansion chamber significantly reduces the likelihood of vapor and aerosol leakage during preparation.

Each of the components described above utilizes the "double membrane" system. The "Protector" vial cover, the "Connector Luer Lock" and the "Infusion Adapter" each have a female bayonet connector fitting. The female bayonet cavity has a hollow tubular side wall and a bottom wall with an elastomeric self-sealing membrane installed therein through which a needle can be passed. The bottom end of the "Injector Luer" encapsulated cannula has a male bayonet fitting with a self-sealing membrane at the tip end, and is designed to be received in the female bayonet connector fitting of either of the "Protector" vial cover, the "Connector Luer Lock" or the "Infusion Adapter", such that the elastomeric self-sealing membranes of the male and female components are resiliently engaged face to face. Transfer is made via a specially cut injection cannula. When the components are separated after transfer, the membranes act as tight seals to prevent leakage and spreading of aerosols or vapor.

The closed system for the preparation and administration of cytotoxic drugs, as described above, is a significant improvement, and is effective provided that the drug is a one-time dose, where the remainder of drug in the vial is discarded, or that additional medications are not added to the I.V. bag before infusion to the patient. However, in many cases the cytotoxic drugs, themselves, may become contaminated due to the manner in which they are handled before and after infusion.

In U.S. hospitals, cytotoxic drugs must be taken out of the safety cabinet or safety hood and transported to another location to be checked by a registered pharmacist. In some instances, a vial containing a remainder of the drug may be placed in storage for future use. In many instances, additional medications are required to be added to the I.V. bag before infusion to the patient. In these situations the female bayonet cavity of the connectors are only sealed by the small elastomeric self-sealing membrane in its bottom wall, and the interior surfaces of the tubular cavity and outer face of the self-sealing membrane are exposed to the environment and can become contaminated. This can also cause contamination of the cytotoxic drug when the male bayonet fitting is installed into the contaminated female bayonet connector, and transfer is made via the injection cannula.

The present invention is distinguished over the prior art in general and these patents in particular by a plug and sealing system for medical bayonet connectors and drug infusion ports of the type having an interior self-sealing element, wherein a male plug removably installed in the female collar portion of the connector, before or after penetration of the self-sealing element by a puncturing needle, has a shank portion the fits the inner surfaces of the collar portion side wall to provide a substantial sealing relation therebetween to prevent contamination of the interior surfaces of the collar portion from environmental contaminants. The plug has a bottom end that is resiliently engaged on an outer face of the self-sealing element, and a pair of lugs that are resiliently biased against a top wall of diametrically opposed apertures in the side wall of the collar portion to maintain the bottom end in a firm sealing relation with the self-sealing element to prevent leakage and spreading of aerosols and vapor.

SUMMARY OF THE INVENTION

It is therefore an object of the present invention to provide a plug for medical bayonet connectors and drug infusion ports that will prevent contamination of the interior surfaces of the female bayonet collar from environmental contaminants.

It is another object of this invention to provide a plug for medical bayonet connectors and drug infusion ports that will engage a self-sealing plug or membrane in the female bayonet collar portion the connector in a sealing relation, before or after penetration by a puncturing needle, to prevent leakage and spreading of aerosols or vapor.

Another object of this invention is to provide a plug for medical bayonet connectors and drug infusion ports that can be quickly and easily installed in the female bayonet collar portion of a vial transfer adapter attached to a drug vial, an intravascular administration connector attached to an I.V. bag, or a connector that attaches to a patient's I.V. tubing.

Another object of this invention is to provide a medical bayonet connector sealing system that will prevent contamination of the interior surfaces of the female bayonet collar from environmental contaminants and engage a self-sealing plug or membrane in the female bayonet collar in a sealing relation, before or after penetration by a puncturing needle, to prevent leakage and spreading of aerosols or vapor.

A further object of this invention is to provide a plug for medical bayonet connectors and drug infusion ports that will not become accidentally loosened or dislodged from the connector.

A still further object of this invention is to provide a plug for medical bayonet connectors and drug infusion ports that is simple in construction, inexpensive to manufacture, rugged and reliable in use, and disposable after use.

Other objects of the invention will become apparent from time to time throughout the specification and claims as hereinafter related.

The above noted objects and other objects of the invention are accomplished by the present plug and sealing system for medical bayonet connectors and drug infusion ports of the type having an interior self-sealing element, wherein a male plug removably installed in the female collar portion of the connector, before or after penetration of the self-sealing element by a puncturing needle, has a shank portion the fits the inner surfaces of the collar portion side wall to provide a substantial sealing relation therebetween to prevent contamination of the interior surfaces of the collar portion from environmental contaminants. The plug has a bottom end that is resiliently engaged on an outer face of the self-sealing element, and a pair of lugs that are resiliently biased against a top wall of diametrically opposed apertures in the side wall of the collar portion to maintain the bottom end in a firm sealing relation with the self-sealing element to prevent leakage and spreading of aerosols and vapor.

DESCRIPTION OF THE PREFERRED EMBODIMENT

Figure 1:
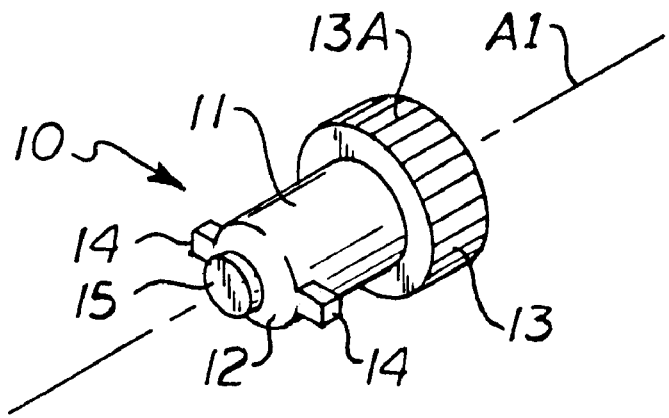
FIG. 1 is a perspective view of the plug for medical bayonet connectors and drug infusion ports in accordance with the present invention shown from the front.
Figure 2:
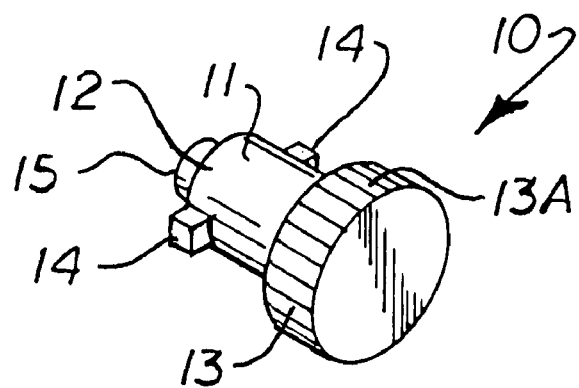
FIG. 2 is a perspective view of the plug for medical bayonet connectors and drug infusion ports shown from the rear.

Referring to the drawings by numerals of reference there is shown in FIGS. 1 and 2, a preferred plug 10 for medical bayonet connectors and drug infusion ports in accordance with the present invention. The plug 10 has a longitudinal cylindrical shank portion 11 extending along a longitudinal axis A1 with a flat bottom end 12 and an enlarged diameter finger grip portion 13 at a top end. Pair of small protrusions or lugs 14 disposed a short distance from the bottom end 12 protrude laterally outward short distance from the shank portion 11 in diametrically opposed relation. The plug 10 is an integrally molded member formed of relatively stiff resilient material.

Preferably, the outer surface of the finger grip portion 13 is provided with a series of circumferentially spaced parallel grooves and ridges 13A or may be otherwise knurled or textured to reduce slipping when the plug is gripped and rotated about its longitudinal axis.

The center of the flat bottom end 12 may be provided with a short reduced diameter disk-like protrusion 15. The exterior of the shank portion 11 of the plug 10 is sized to closely fit the inner surfaces of a female bayonet collar portion of a medical connector or infusion port (described below) and the protrusion 15 is sized to engage the outer facing surface of a self-sealing plug or membrane disposed in a bottom wall of the female bayonet collar portion through which a needle is to be passed. Depending upon the material used to form the plug 10, the protrusion 15 may be integrally molded with the plug, or may be a separate element formed of a more resilient material that is secured to or in the flat bottom end 12 of the plug. For example, the protrusion 15 may be formed of the same material as the self-sealing plug or membrane disposed in the female bayonet collar. The disk-shaped protrusion 15 may also be of a diameter larger than the self-sealing plug or membrane in the female collar so as to compress the resilient self-sealing plug or membrane and engage the surrounding bottom wall of the female bayonet collar portion.

Also, depending upon the resiliency of the material used to form the plug 10 and the self-sealing plug or membrane in the female bayonet collar portion, the plug may be provided without a disk-shaped protrusion wherein the flat bottom end 12 will compress the resilient self-sealing plug or membrane and engage the surrounding bottom wall of the female bayonet collar portion.

Figure 3:
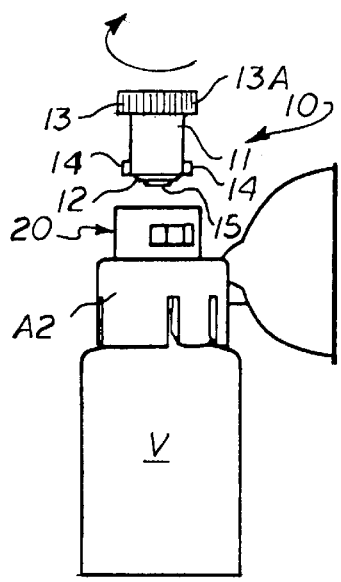
FIG. 3 is a side elevation of the plug being installed in the female bayonet collar portion of a vial transfer adapter attached to a drug vial.
Figure 4:
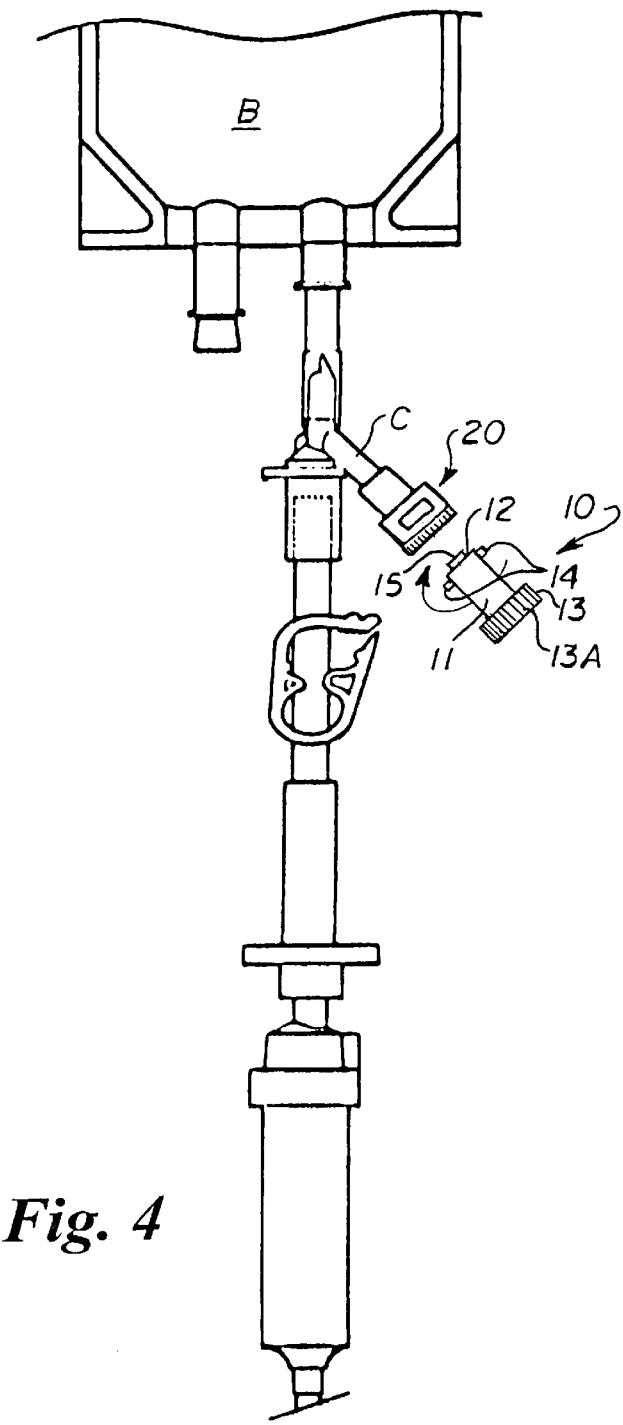
FIG. 4 is a side elevation of the plug being installed in the female bayonet collar portion of an intravascular administration connector attached to an I.V. bag.

FIG. 3 shows the plug 10 being installed in the female bayonet collar portion 20 of a vial transfer adapter A2 attached to a drug vial V and FIG. 4 shows the plug being installed in the female bayonet collar portion 20 of an intravascular administration connector C attached to an I.V.

bag B. The plug 10 may also be installed in a female bayonet collar portion of a connector that attaches to a patient's I.V. tubing which has the same collar portion configuration as the collar portion of the vial transfer adapter and the intravascular administration connector described above.

Figure 5:
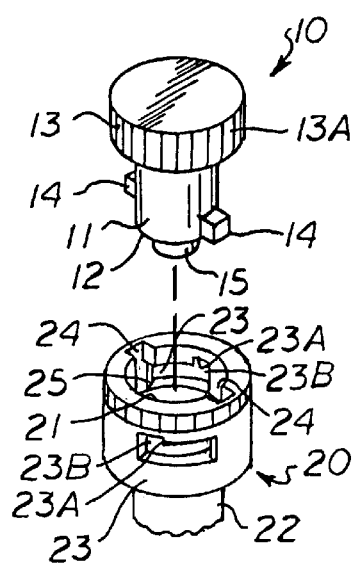
FIG. 5 is a perspective view of the plug being installed in a female bayonet collar.
Figure 6:
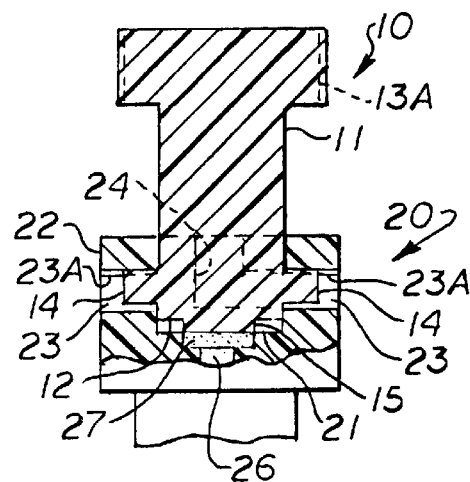
FIG. 6 is a side elevation of the plug installed in a sealing relation in a female bayonet collar.

FIGS. 5 and 6 more clearly show the female bayonet collar 20. The collar 20 has a bottom wall 21 and a circumferential tubular side wall 22 extending therefrom with an inside and an outside surface and an open top end. A pair of circumferential arcuate cutouts or apertures 23 are formed in the side wall 22 in diametrically opposed relation. A pair of generally circular J-shaped bayonet channels are formed on the inside of the collar 20 in diametrically opposed relation. Each channel has a vertical slot portion 24 extending downwardly a distance from the open top end and terminating in a short arcuate channel portion 25 which opens into one side of the respective aperture 23. The vertical dimension of each aperture 23 is greater near its end opposite the short channel portion 24 to define a small vertical shoulder 23A and a larger end portion 23B.

The vertical slot portions 24 receive the lugs 14 of the plug 10 during installation and the short arcuate channel portions 25 and apertures 23 extend in a circumferential direction to enable a slight circumferential twisting action of the plug to take place during locking and unlocking of the plug 10 to the collar 20.

As best seen in FIG. 6, the bottom wall 21 of the collar 20 has a central aperture 26 which is sealed at its top end by a self-sealing elastomeric plug or membrane 27 through which a puncturing needle can be passed. Typically the self-sealing elastomeric plug or membrane 27 is formed of Teflon®, but may be formed of other material which seals itself tight after penetration by a puncturing needle. Typically the self-sealing elastomeric plug or membrane 27 has an outer face which protrudes a short distance above the surface of the bottom wall 21 of the collar portion of the connector when not compressed.

The plug 10 is installed in the collar 20, before or after penetration of the self-sealing plug or membrane 27 by a puncturing needle, by placing the lugs 14 into the vertical slots 24 and pressing it axially into the collar until the lugs engage the short arcuate channel portions 25 and the disk-like protrusion 15 at the bottom end 12 of the plug engages the resilient plug or membrane 27 and then twisting the plug 10 it about its longitudinal axis until the lugs enter the arcuate cut-outs or apertures 23. Due to the resiliency of the resilient plug or membrane 27, the lugs 14 are resiliently biased against the top surface of the respective apertures 23 and ride thereon until they pass over the small vertical shoulder 23A and snap into the larger end portion 23B of the aperture to lock the plug into the collar. The process described above is reversed to unlock the plug 10 from the collar 20.

As shown in FIG. 6, in the installed and locked position, the exterior of the shank portion 11 of the plug 10 closely fits the inner surfaces of the collar 20 to provide a substantial sealing relation therebetween, the protrusion 15 is resiliently engaged on the outer face of the resilient self-sealing plug or membrane 27 in face to face relation, and the lugs 14 are resiliently biased against the top wall of the apertures 23 to maintain the protrusion 15 in a firm sealing relation with the self-sealing plug or membrane.

As described previously, depending upon the material used to form the plug 10, the protrusion 15 may be integrally molded with the plug, or may be a separate element formed of a more resilient material that is secured to or in the flat bottom end 12 of the plug. The disk-shaped protrusion 15 may also be of a diameter larger than the self-sealing plug or membrane 27 in the female collar so as to compress the resilient self-sealing plug or membrane and engage the surrounding bottom wall 21 of the female bayonet collar portion. Also, depending upon the resiliency of the material used to form the plug 10 and the self-sealing plug or membrane 27, the plug 10 may be provided without a disk-shaped protrusion wherein its flat bottom end 12 will compress the resilient self-sealing plug or membrane 27 and engage the surrounding bottom wall 21 the collar 20 in a sealing relation.

While this invention has been described fully and completely with special emphasis upon a preferred embodiment, it should be understood that within the scope of the appended claims the invention may be practiced otherwise than as specifically described herein.

What is claimed is:

1. A male plug for removable installation in a female collar portion of a medical bayonet connector of the type having an interior self-sealing element, to seal the element before or after penetration by a puncturing needle to prevent leakage and spreading of aerosols and vapor and to prevent contamination of the interior surfaces of the collar portion from environmental contaminants, comprising;

a male plug having a longitudinal solid cylindrical shank portion extending along a longitudinal axis and having no interior cavities;

a flat bottom end on said shank portion;

an enlarged diameter finger grip portion at a top end of said shank portion; and a pair of small lugs formed on said shank portion disposed a short distance from said bottom end protruding laterally outward a short distance from said shank portion in diametrically opposed relation;

said shank portion, said finger grip portion, and said pair of small lugs integrally formed of stiff resilient material.

2. The plug according to claim 1, further comprising:

a disk-shaped protrusion on said flat bottom end having a diameter smaller than the diameter of said shank portion and protruding a short distance from said flat bottom end.

3. The plug according to claim 2, wherein said disk-shaped protrusion is formed of a resilient material.

4. The plug according to claim 2, wherein said shank portion, said finger grip portion, said pair of small lugs, and said disk-shaped protrusion are integrally formed of stiff resilient material.

5. A male plug for removable installation in a female collar portion of a medical bayonet connector of the type having an interior self-sealing element, to seal the element before or after penetration by a puncturing needle to prevent leakage and spreading of aerosols and vapor and to prevent contamination of the interior surfaces of the collar portion from environmental contaminants, comprising;

a male plug having a longitudinal solid cylindrical shank portion extending along a longitudinal axis and having no interior cavities;

a flat bottom end on said shank portion;

an enlarged diameter finger grip portion at a top end of said shank portion;

a pair of small lugs formed on said shank portion disposed a short distance from said bottom end protruding laterally outward a short distance from said shank portion in diametrically opposed relation; and a disk-shaped protrusion on said flat bottom end having a diameter smaller than the diameter of said shank portion and protruding a short distance from said flat bottom end;

said shank portion, said finger grip portion, and said pair of small lugs integrally formed of a stiff resilient material; and said disk-shaped protrusion formed of a resilient material more resilient than said stiff resilient material.

6. A medical bayonet connector sealing system, comprising in combination;

a connector member having a first end with a tubular female bayonet collar portion, said collar portion having an open top end and a circumferential tubular side wall with an inside surface, a lower wall in said collar portion disposed a distance from said top end, a pair of circumferential arcuate apertures in said side wall disposed in diametrically opposed relation, and a pair of generally circular J-shaped bayonet channels formed on said inside surface in diametrically opposed relation, each of said channels having a vertical slot portion extending downwardly a distance from said open top end and terminating in a short arcuate channel portion that opens into a first side of a respective said aperture, each of said apertures having a smaller vertical opening extending circumferentially from said first side and terminating in a larger vertical opening at a second side to define a top surface with a small vertical shoulder between said smaller and larger openings;

a central aperture in said lower wall extending to a second end of said collar portion;

a resilient self-sealing element in said central aperture through which a puncturing needle can be passed; and a male plug integrally formed of stiff resilient material having a longitudinal solid cylindrical shank portion extending along a longitudinal axis and having no interior cavities, a flat bottom end, an enlarged diameter finger grip portion at a top end, and a pair of small lugs disposed a short distance from said bottom end protruding laterally outward a short distance from said shank portion in diametrically opposed relation; wherein said male plug is installed in said collar portion, before or after penetration of said self-sealing element by a puncturing needle, by placing said lugs into respective said vertical slot portions and pressing it axially into said collar until said lugs engage said short arcuate channel portions and said bottom end engages said self-sealing element and then twisting said plug about its longitudinal axis until said lugs enter said arcuate apertures such that said lugs are resiliently biased against said top surface of said apertures and ride thereon until they pass over said small vertical shoulder and snap into said larger vertical opening to lock said plug into said collar portion, and the process just described is reversed to unlock said male plug from said collar portion; and in the installed and locked position, said solid cylindrical shank portion fits said inner surface of said collar portion side wall to provide a substantial sealing relation therebetween to prevent contamination of the interior surfaces of said collar portion from environmental contaminants, said bottom end is resiliently engaged on an outer face of said self-sealing element, and said lugs are resiliently biased against said top wall of said apertures to maintain said bottom end in a firm sealing relation with said self-sealing element to prevent leakage and spreading of aerosols and vapor.

7. The medical bayonet connector sealing system according to claim 6, wherein;

said connector member second end is attached or connectable to a vessel.

8. The medical bayonet connector sealing system according to claim 6, wherein;

said connector member second end is attached or connectable to an intravascular administration connector for an I.V. bag.

9. The medical bayonet connector sealing system according to claim 6, wherein;

said connector member second end is attached or connectable to a section of I.V. tubing.

10. The medical bayonet connector sealing system according to claim 6, wherein said male plug shank portion has a disk-shaped protrusion having a diameter smaller than the diameter of said shank portion and protruding a short distance from said flat bottom end.

11. The medical bayonet connector sealing system according to claim 10, wherein said disk-shaped protrusion is formed of a resilient material.

12. The medical bayonet connector sealing system according to claim 10, wherein said male plug shank portion is a solid cylindrical portion, and said shank portion, said finger grip portion, said pair of small lugs, and said disk-shaped protrusion are integrally formed of stiff resilient material.

13. The medical bayonet connector sealing system according to claim 10, wherein said male plug shank portion is a solid cylindrical portion, said shank portion, said finger grip portion, and said pair of small lugs are integrally formed of a stiff resilient material, and said disk-shaped protrusion is formed of a resilient material more resilient than said stiff resilient material.

* * * * *